(12) United States Patent
Han et al.

(10) Patent No.: US 7,094,427 B2
(45) Date of Patent: Aug. 22, 2006

(54) COMBINATION IMMEDIATE RELEASE CONTROLLED RELEASE LEVODOPA/CARBIDOPA DOSAGE FORMS

(75) Inventors: Chien-Hsuan Han, Sunnyvale, CA (US); Larry Hsu, Los Altos Hills, CA (US); Ann F. Hsu, Los Altos Hills, CA (US)

(73) Assignee: Impax Laboratories, Inc., Hayward, CA (US)

( * ) Notice: Subject to any disclaimer, the term of this patent is extended or adjusted under 35 U.S.C. 154(b) by 0 days.

(21) Appl. No.: 10/241,837

(22) Filed: Sep. 12, 2002

(65) Prior Publication Data
US 2003/0228360 A1    Dec. 11, 2003

Related U.S. Application Data

(63) Continuation-in-part of application No. 10/158,412, filed on May 29, 2002, now abandoned.

(51) Int. Cl.
*A61K 9/24* (2006.01)
*A61K 9/48* (2006.01)
*A61K 9/20* (2006.01)
*A61K 9/22* (2006.01)
*A61K 9/14* (2006.01)

(52) U.S. Cl. ............... 424/472; 424/451; 424/456; 424/464; 424/465; 424/468; 424/474; 424/484; 424/489

(58) Field of Classification Search ........... 424/451, 424/456, 464, 465, 468, 472, 474, 484, 489
See application file for complete search history.

(56) References Cited

U.S. PATENT DOCUMENTS

| | | | |
|---|---|---|---|
| 3,891,696 A | * | 6/1975 | Bodor et al. |
| 4,021,555 A | | 5/1977 | Seyfried et al. |
| 4,160,020 A | | 7/1979 | Ayer et al. |
| 4,424,235 A | | 1/1984 | Sheth et al. |
| 4,832,957 A | | 5/1989 | Dempski et al. |
| 4,839,177 A | | 6/1989 | Colombo et al. |
| 4,900,755 A | * | 2/1990 | Dempski et al. |
| 4,963,590 A | | 10/1990 | Backstrom et al. |
| 5,112,861 A | | 5/1992 | Backstrom et al. |
| 5,135,950 A | | 8/1992 | Pippuri et al. |
| 5,188,840 A | | 2/1993 | Iida et al. |
| 5,652,271 A | | 7/1997 | Harris et al. |
| 5,738,874 A | * | 4/1998 | Conte et al. |
| 5,945,424 A | | 8/1999 | Schmidt |
| 6,238,699 B1 | * | 5/2001 | Rubin |
| 6,294,200 B1 | * | 9/2001 | Conte et al. |
| 6,500,867 B1 | | 12/2002 | Virkki et al. |
| 6,797,732 B1 | | 9/2004 | Virkki et al. |

FOREIGN PATENT DOCUMENTS

| | | |
|---|---|---|
| WO | WO 95/01781 A | 1/1995 |
| WO | 99/17745 * | 4/1999 |
| WO | WO 99/17745 | 4/1999 |

OTHER PUBLICATIONS

Grahnén et al., "Comparative Multiple-Dose Pharmacokinetics of Controlled-Release Levodopa Products," Eur. Neurol. 1992:32; pp. 343-348.

(Continued)

*Primary Examiner*—Humera N. Sheikh

(57) ABSTRACT

The present invention relates to dosage forms of a combination of carbidopa and levodopa comprising both immediate release and controlled release components for the treatment of ailments associated with depleted amounts of dopamine in a patient's brain tissue.

31 Claims, 6 Drawing Sheets

OTHER PUBLICATIONS

Stocchi et al., "Comparison Between a Fast and a Slow Release Preparation of Levodopa and a Combination of the Two: A Clinical and Pharmacokinetic Study," Clinical Neuropharmacology, vol. 17, No. 1, pp. 38-44.

Stocchi et al., "Clinical Implications of Sustained Dopaminergic Stimulation," Clinical Neuropharmacology, vol. 17, Suppl. 2, pp. S7-S13.

Stocchi et al., "Clinical Efficacy of Single Morning Doses of Different Levodopa Formulations," Clinical Neuropharmacology, vol. 17, Suppl. 3, pp. S16-S20.

Harder et al., "Concentration-Effect Relationship of Levodopa in Patients with Parkinson's Disease After Oral Administration of an Immediate Release and a Controlled Release Formulation," Br. J. Clin. Pharmac. 1995; 39: pp. 39-44.

Fassihi et al., "Multiple-Layer, Direct-Compression, Controlled-Release System: In Vitro and In Vivo Evaluation," Journal of Pharmaceutical Sciences, vol. 82, No. 7, Jul. 1993, pp. 750-754.

Ghika et al., "Clinical Efficacy and Tolerability of a New Levodopa/Benserazide Dual-Release Formulation in Parkinsonian Patients," Clinical Neuropharmacology, vol. 20, No. 2, pp. 130-139.

Gasser et al., "Comparative Single- and Multiple-Dose Pharmacokinetics of Levodopa and 3-O-Methyldopa Following a New Dual-Release and a Conventional Slow-Release Formulation of Levodopa and Benserazide in Healthy Subjects," European Journal of Pharmaceutics and Biopharmaceutics 46 (1998) pp. 223-228.

Descombes et al., "Dual-Release Formulation, A Novel Principle in L-dopa Treatment of Parkinson's Disease," Neurology 56, May (1 of 2) 2001, pp. 1239-1242.

Roger Kurlan et al., "Duodenal and Gastric Delivery of Levodopa in Parkinsonism," American Neurological Association, 1988.

John G. Nutt et al., "Review, Pharmacokinetics of Levodopa," Clinical Neuropharmacology, vol. 7, No. 1, pp. 35-49, 1984 Raven Press, New York.

R. Kurlan, et al., "Erratic gatric emptying of levodopa may cause "random" fluctuations of parkinsonianmobility," Neurology, Mar. 1988.

* cited by examiner

COMBINATION IMMEDIATE RELEASE CONTROLLED RELEASE LEVODOPA/CARBIDOPA DOSAGE FORMS

This application claims the benefit under 35 U.S.C. § 120 of U.S. patent application Ser. No. 10/158,412 filed on May 29, 2002, now abandoned, by Chien-Hsuan Han et al., entitled Combination Immediate Release Sustained Release Levodopa/Carbidopa Dosage Forms, which is incorporated herein by reference in its entirety.

FIELD OF THE INVENTION

The present invention relates to dosage forms of a combination of carbidopa and levodopa comprising both immediate release and controlled release components for the treatment of ailments associated with depleted amounts of dopamine in a patient's brain tissue.

BACKGROUND

Combinations of carbidopa and levodopa to treat Parkinson's disease are known in the pharmaceutical arts. Several products currently on the North American market, including SINEMET® (Merck Co.) and SINEMET® (Merck Co.) CR contain combinations of carbidopa and levodopa in immediate release and controlled release forms, respectively. Overseas, other decarboxylase inhibitor and levodopa combinations include those sold under the mark Madopark (levodopa with benserizide instead of carbidopa).

The carbidopa and levodopa combination is used to treat the symptoms of Parkinson's disease, which is characterized by abnormally low levels of dopamine. Dopamine is a neurotransmitter having significant influence over the mobility and control of the skeletal muscular system. Patients suffering from Parkinson's disease frequently have periods in which their mobility becomes difficult, often resulting in an inability to move.

Administering dopamine is not effective to treat Parkinson's disease because dopamine does not cross the blood brain barrier. To resolve this failure, Parkinson's patients are administered levodopa, the metabolic precursor of dopamine. Levodopa crosses the blood brain barrier and is rapidly converted to dopamine, thereby alleviating the symptoms of Parkinson's disease caused by reduced levels of dopamine. Levodopa is problematic because of its rapid decarboxylation by tissues other than the brain. Thus, when levodopa is administered alone, large doses are required because only a small portion is transported to the brain unchanged.

Patients treated with levodopa therapy for Parkinson's disease may frequently develop motor fluctuations characterized by end-of-dose failure, peak dose dyskinesia and akinesia. An advanced form of motor fluctuations is known as the "on-off effect" in which the patient suffers from unpredictable swings from mobility to immobility. It is believed that the on-off effect can be minimized in some patients with a treatment regimen which produces narrow ranges of plasma levels of levodopa.

Carbidopa inhibits the decarboxylation of levodopa by a patient's body tissues outside of the brain. Small doses of carbidopa administered in conjunction with levodopa allow a larger percentage of levodopa to reach the brain unchanged for later conversion to dopamine. There is at least one study reporting that carbidopa reduces the amount of levodopa required to produce a given response by about 75% and, when administered in conjunction with levodopa, increases plasma levels and the plasma half life of levodopa. The carbidopa and levodopa combination allows for lower doses of levodopa with a concordant reduction of side effects.

The carbidopa and levodopa combination is now available in immediate release as well as controlled release compositions. The controlled release formulations allow for the continuous release of drug over a prolonged period in an attempt to maintain tight levodopa plasma ranges. However, the use of controlled release dosage forms are problematic in that many Parkinson's patients wake up in the morning having little or no mobility due to the wearing off of the previous dose taken the day or evening before. Once the previous dose has worn off, such patients are usually unwilling or unable to wait for the extended period of time required for a controlled release dosage form to deliver the appropriate plasma levels of levodopa. The use of immediate release formulations require more frequent dosing and are associated with more fluctuating plasma levodopa concentrations.

Combination immediate release and controlled release carbidopa and levodopa dosage forms are described in U.S. Pat. No. 6,238,699 to Rubin, entitled Pharmaceutical Formulations Containing A Combination Of Carbidopa And Levodopa, issued May 29, 2001, which discloses an immediate release and controlled release carbidopa and levodopa combination product, and is incorporated herein by reference.

There remains, however, a continuing need for immediate release and controlled release carbidopa and levodopa products which will improve the administration of levodopa to Parkinson's patients by narrowing blood plasma ranges of levodopa and reducing side effects.

SUMMARY OF THE INVENTION

The present invention is directed to a pharmaceutical dosage form having an immediate release component and a controlled release component. The immediate release component comprises a ratio of carbidopa to levodopa of from about 1:1 to about 1:50 such that the in vitro dissolution rate of the immediate release component is from about 10% to about 99% levodopa released after 15 minutes and from about 60% to about 99% levodopa released after 1 hour. The controlled release component comprises a ratio of carbidopa to levodopa of from about 1:1 to about 1:50 such that the in vitro dissolution rate of the controlled release component is from about 10% to about 60% levodopa released after 1 hour; from about 20% to about 80% levodopa released after 2 hours; and from about 30% to about 99% levodopa released after about 6 hours according to measurements under the USP paddle method of 50 rpm in 900 ml aqueous buffer at pH 4 at 37° C. The in vitro release rate is chosen such that the initial peak plasma level of levodopa obtained in vivo occurs between 0.1 and 6 hours after administration of the dosage form.

DETAILED DESCRIPTION OF THE PREFERRED EMBODIMENTS

Figure 1:
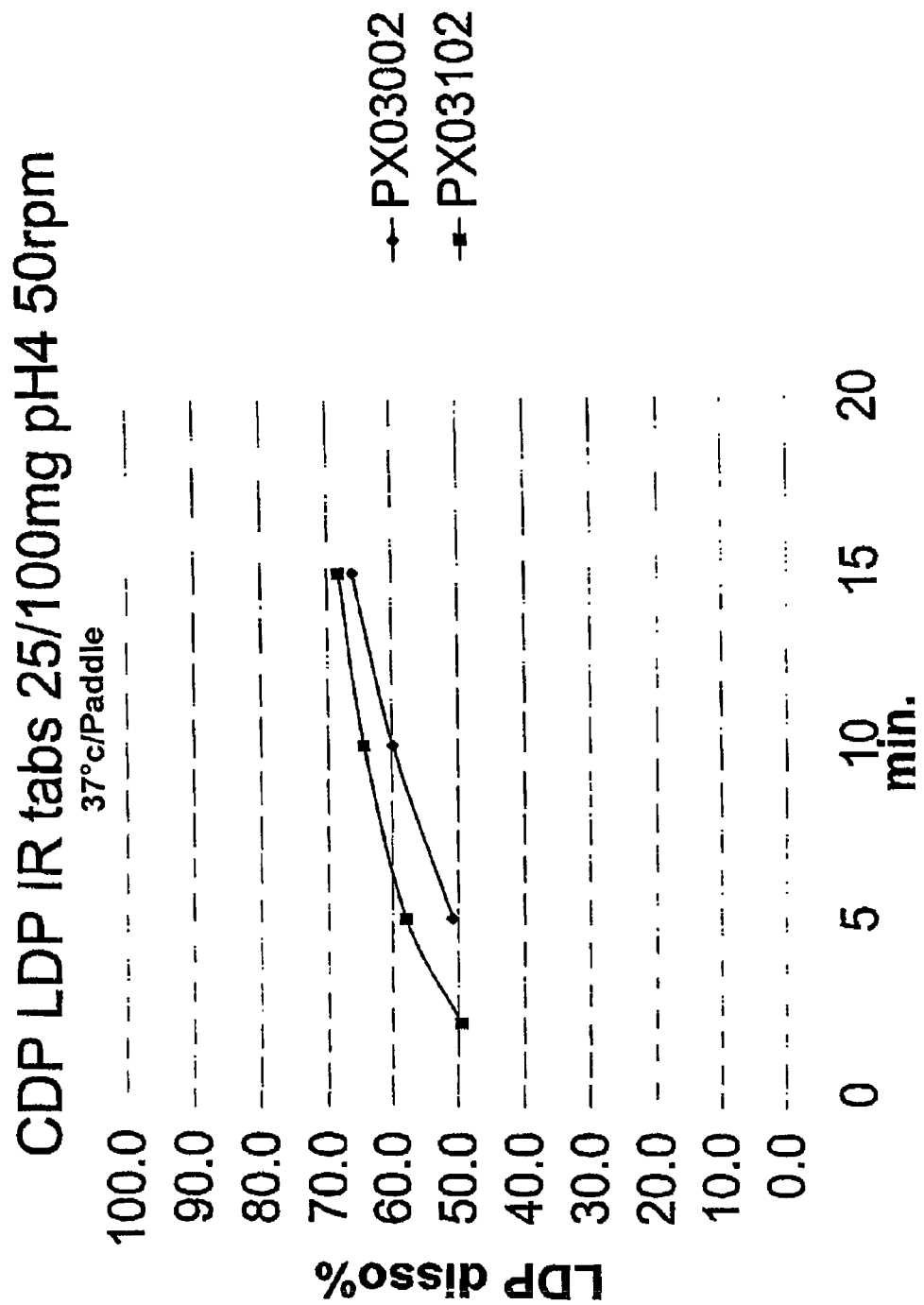
FIG. 1 is a graph of the dissolution profiles of carbidopa/levodopa immediate release (IR) 25/100 mg formulations PX03002 and PX03102 according to measurements under the USP paddle method of 50 rpm in 900 ml acetate buffer at pH 4 at 37° C.

The present invention is directed to methods of treating symptoms, pathologies or diseases characterized by reduced levels of dopamine in a patients brain, including neurological or movement disorders such as restless leg syndrome, Parkinson's disease and secondary parkinsonism, Huntington's disease, Shy-Drager syndrome and conditions resulting from brain injury including carbon monoxide or manganese intoxication.

The present invention is directed to a pharmaceutical dosage form having an immediate release component and a controlled release component. The immediate release component comprises carbidopa alone or a ratio of carbidopa to levodopa from about 1:1 to about 1:50 such that the in vitro dissolution rate of the immediate release component, according to measurements under the USP paddle method of 50 rpm in 900 ml aqueous buffer at pH 4 at 37° C., is from about 10% to about 99% active agent released after 15 minutes and from about 75% to about 99% active agent released after 1 hour. Benzeraside as an alternate peripheral decarboxylase inhibitor, and may be substituted in appropriate doses in all subsequent details of the carbidopa discussions. The controlled release component comprises a ratio of levodopa to carbidopa of from about 1:2 to about 1:50 such that the in vitro dissolution rate of the controlled release component, according to measurements under the USP paddle method of 50 rpm in 900 ml aqueous buffer at pH 4 at 37° C., is about 10% to about 60% levodopa released after 1 hour; from about 25% to about 80% levodopa released after 2 hours; and, from about 40% to about 95% levodopa released after 6 ours. Additionally, the formulations of the present invention are chosen such that the initial peak plasma level of levodopa obtained in vivo occurs between 0.1 and 6 hours after administration of the dosage form.

The ratio of immediate release to controlled release Levodopa in dosage forms according to the present invention is from about 3 to about 0.1. The skilled artisan will appreciate that this ratio can range anywhere within these endpoints depending on the goal of therapy and such well known factors such as patient weight, stage of disease, etc. The skilled artisan will appreciate that the ratios of 1, 0.875, 0.538, 0.5 and 0.33, which are used in dosage forms according to the present invention, are representative of specific ratios, but not limiting of the possible ratios which may be employed in carbidopa/levodopa dosage forms.

For purposes of the present invention the term "controlled release" refers to a pharmaceutical dosage form which releases one or more active pharmaceutical agents over a prolonged period of time, in this case over a period of more than 1 hour. Controlled release (CR) components can also be referred to as sustained release (SR), prolonged release (PR), or extended release (ER). When used in association with the dissolution profiles discussed herein, the term "controlled release" refers to that portion of a dosage form made according to the present invention which delivers active agent over a period of time greater than 1 hour.

"Immediate release" refers to a dosage form which releases active agent substantially immediately upon contact with gastric juices and will result in substantially complete dissolution within about 1 hour. Immediate release (IR) components can also be referred to as instant release. When used in association with the dissolution profiles discussed herein, the term "immediate release" refers to that portion of a dosage form made according to the present invention which delivers active agent over a period of time less than 1 hour.

Initial peak plasma level refers to the first rise in blood plasma level of active agent and may be followed by one or more additional peaks, one of which may be $C_{max}$.

The USP paddle method refers to the Paddle and Basket Method as described in United States Pharmacopoeia, Edition XXII (1990).

As used herein, the term patient means any mammal including humans.

The active agents for use in dosage forms according to the present invention include levodopa and carbidopa their salts, derivatives and pro-drugs. The terms "levodopa" and "carbidopa" are meant to embrace these chemical compounds themselves, pro-drugs thereof, N-oxides thereof, the pharmaceutically acceptable salts thereof, derivatives thereof, and the solvates thereof, e.g. hydrates, where the context so permits. Similarly, reference to intermediates, whether or not they themselves are claimed, is meant to embrace their salts, and solvates, where the context so permits.

The term "derivative" means a chemically modified compound wherein the modification is considered routine by the ordinary skilled chemist, such as an ester or an amide of an acid, protecting groups, such as a benzyl group for an alcohol or thiol, and tert-butoxycarbonyl group for an amine.

The term "effective amount" means an amount of a compound/composition according to the present invention effective in producing the desired therapeutic effect.

The term "analogue" means a compound which comprises a chemically modified form of a specific compound or class thereof, and which maintains the pharmaceutical and/or pharmacological activities characteristic of said compound or class.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quarternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluensulfonic, methanesulfonic, ethane dislfonic, oxalic, isethionic, and the like.

The phrase "pharmaceutically acceptable" is employed herein to refer to those compounds, materials, compositions; and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

The term "about" when used in connection with percentages means±1%.

The term "Pro-drugs", as the term is used herein, is intended to include any covalently bonded carriers which release an active parent drug of the present invention in vivo when such pro-drug is administered to a mammalian subject. Since pro-drugs are known to enhance numerous desirable qualities of pharmaceuticals (i.e., solubility, bioavailability, manufacturing, etc.) the compounds of the present invention may be delivered in pro-drug form. Thus, the present invention is intended to cover pro-drugs of the presently claimed compounds, methods of delivering the same, and compositions containing the same.

One example of a pro-drug for levodopa is 3-hydroxy-L-tyrosine ethyl ester. In the formulations of the present invention, 3-hydroxy-L-tyrosine ethyl ester can be used in combination with levodopa or as a replacement for levodopa in any of the formulations. Generally, an appropriate pro-drug for levodopa can be used in combination with levodopa or as a replacement for levodopa in any of the levodopa/carbidopa formulations of the present invention. Similarly, an appropriate pro-drug for carbidopa can be used in combination with levodopa or as a replacement for carbidopa in any of the levodopa/carbidopa formulations of the present invention.

Pro-drugs of the present invention are prepared by modifying functional groups present in the compound in such a way that the modifications are cleaved, either in routine manipulation or in vivo, to the parent compound. The transformation in vivo may be, for example, as the result of some metabolic process, such as chemical or enzymatic hydrolysis of a carboxylic, phosphoric or sulphate ester, or reduction or oxidation of a susceptible functionality. Pro-drugs within the scope of the present include compounds wherein a hydroxy, amino, or sulfhydryl group is bonded to any group that, when the pro-drug of the present invention is administered to a mammalian subject, it cleaves to form a free hydroxyl, free amino, or free sulfydryl group respectively. Functional groups which may be rapidly transformed, by metabolic cleavage, in vivo form a class of groups reactive with the carboxyl group of the compounds of this invention. They include, but are not limited to such groups as alkanoyl (such as acetyl, propionyl, butyryl, and the like), unsubstituted and substituted aroyl (such as benzoyl and substituted benzoyl), alkoxycarbonyl (such as ethoxycarbonyl), trialkysilyl (such as trimethyl- and triethysilyl), monoesters formed with dicarboxylic acids (such as succinyl), and the like. Because of the ease with which metabolically cleavable groups of the compounds useful according to this invention are cleaved in vivo, the compounds bearing such groups act as pro-drugs. The compounds bearing the metabolically cleavable groups have the advantage that they may exhibit improved bioavailability as a result of enhanced solubility and/or rate of absorption conferred upon the parent compound by virtue of the presence of the metabolically cleavable group.

A thorough discussion of pro-drugs is provided in the following: Design of Pro-drugs, H. Bundgaard, ed., Elsevier, 1985; Methods in Enzymology, K. Widder et al., ed., Academic Press, 42, p. 309–396, 1985; A Textbook of Drug Design and Development, Krogsgaard-Larsen and H. Bundgaard, ed., Chapter 5; "Design and Applications of Pro-drugs" p. 113–191, 1991; Advanced Drug Delivery Reviews, H. Bundgard, 8, p. 1–38, 1992; Journal of Pharmaceutical Sciences, 77, p. 285, 1988; Chem. Pharm. Bull., N. Nakeya et al., 32, p. 692, 1984; Pro-drugs as Novel Delivery Systems, T. Higuchi and V. Stella, Vol. 14 of the A.C.S. Symposium Series, and Bioreversible Carriers in Drug Design, Edward B. Roche, ed., American Pharmaceutical Association and Pergamon Press, 1987, each of which is incorporated herein by reference.

Total daily dosages of the compounds useful according to this invention administered to a host in single or divided doses are generally in amounts of from about 0.01 mg/kg to about 100 mg/kg body weight daily, and preferably from about 0.05 mg/kg to about 50 mg/kg body weight daily. Both the levodopa and carbidopa doses fall within this mg/kg/day dosage range. The relative amounts of carbidopa and levodopa can vary from about 1:1 to about 1:50 in dosage forms according to the present invention. Other dosage ratios useful according to the present invention include 1:10, 5:26, 1:5, 1:4, 5:16, 1:3, 5:14, 1:2, 2:3, 3:4, 5:6) of carbidopa to levodopa.

The skilled artisan will appreciate that daily dosages having an amount of active agent sufficient to treat Parkinson's disease will generally contain from about 25 mg to about 4,000 mg of levodopa in combination with from about 5 mg to about 600 mg of carbidopa. Dosage forms according to the present invention may also contain from about 25 or preferably 100 mg to about preferably 300 or 600 mg of levodopa in combination with from about 12.5 or preferably 50 mg to about preferably 75 or 200 mg of carbidopa. Preferred dosage forms contain 25, 37.5, 50, 70, 75, 80, 100, 125, 130, 150, 200, 250, 300, 400, or 600 mg of levodopa and 12.5, 25, 37.5, 50, 75, 100, 112.5, 125 or 150 mg of carbidopa. Preferred dosage forms include all possible combinations of these amounts of levodopa and carbidopa. Dosage unit compositions may also contain amounts of levodopa and carbidopa in percentages of these dosages as may be used to make up the daily dose. It will be understood, however, that the specific dose level for any particular patient will depend upon a variety of factors including body weight, general health, gender, diet, time and route of administration, rates of absorption and excretion, combination with other drugs, and the severity of the particular disease being treated.

Actual dosage levels of active ingredient in the compositions of the present invention may be varied so as to obtain an amount of active ingredient that is effective to obtain a desired therapeutic response for a particular composition and method of administration. The selected dosage level, therefore, depends upon the desired therapeutic effect, on the route of administration, on the desired duration of treatment, and other factors.

The dosage forms of the present invention are designed to administer active agent according to the combination of two release profiles. The first profile is an immediate release burst of carbidopa, another decarboxylase inhibitor such as benserazide, or a combination of active ingredients such as a decarboxylase inhibitors and levodopa to provide early relief from symptoms via quick onset of effective blood plasma levels of active agent. Such early release is such that the in vitro dissolution rate of the immediate release component, according to measurements under the USP paddle method of 50 rpm in 900 ml aqueous buffer at pH 4 at 37° C. are from about 10% to about 99% levodopa released after 15 minutes and from about 75% to about 99% levodopa released after 1 hour.

The second profile is a controlled release profile in which the combination of active ingredients is released slowly over time to provide a plasma level effective to alleviate the symptoms of Parkinson's disease over a prolonged period. This controlled release profile may be over a period of 3, 4, 6, 8, 12, or 24 hours. Furthermore, the controlled release profile of the present invention is such that the in vitro dissolution rate of the controlled release component, according to measurements under the USP paddle method of 50 rpm in 900 ml aqueous buffer at pH 4 at 37° C., are from about 10% to about 60% levodopa released after 1 hour; from about 25% to about 80% released after 2 hours; from about 30% to about 85% levodopa released after 4 hours and from about 40% to about 99% levodopa released after about 6 hours, and chosen such that the peak plasma level of levodopa obtained in vivo occurs between 0.1 and 6 hours after administration of the dosage form.

The active ingredients of the present invention may be mixed with pharmaceutically acceptable carriers, diluents, adjuvants, excipients, or vehicles, such as preserving agents, fillers, polymers, disintegrating agents, glidants, wetting agents, emulsifying agents, suspending agents, sweetening agents, flavoring agents, perfuming agents, lubricating agents, acidifying agents, and dispensing agents, depending on the nature of the mode of administration and dosage forms. Such ingredients, including pharmaceutically acceptable carriers and excipients that may be used to formulate oral dosage forms, are described in the Handbook of Pharmaceutical Excipients, American Pharmaceutical Association (1986), incorporated herein by reference in its entirety. Examples of pharmaceutically acceptable carriers include water, ethanol, polyols, vegetable oils, fats, waxes polymers, including gel forming and non-gel forming polymers, and suitable mixtures thereof. Examples of excipients include starch, pregelatinized starch, Avicel, lactose, milk sugar, sodium citrate, calcium carbonate, dicalcium phosphate, and lake blend. Examples of disintegrating agents include starch, alginic acids, and certain complex silicates. Examples of lubricants include magnesium stearate, sodium lauryl sulphate, talc, as well as high molecular weight polyethylene glycols. The artisan of ordinary skill in the art will recognize that many different excipients can be used in formulations according to the present invention and the list provided herein is not exhaustive.

Dosage Forms

Dosage forms can be made according to well known methods in the art. Some preferred methods are described below.

Matrix Dosage Forms

The term matrix, as used herein, is given its well known meaning in the pharmaceutical arts, that is a solid material having an active agent incorporated therein. Upon exposure to a dissolution media, channels are formed in the solid material so that the active agent can escape. Dosage forms according to one embodiment of the present invention may be in the form of coated or uncoated matrices. A coating, for example may contain immediate release carbidopa alone, or in the alternative, a combination of levodopa and carbidopa, and the matrix itself can contain the controlled release combination of levodopa and carbidopa.

The skilled artisan will appreciate that the matrix material can be chosen from a wide variety of materials which can provide the desired dissolution profiles. Materials can include, for example, one or more gel forming polymers such as polyvinyl alcohol, cellulose ethers including, for example, hydroxy propyl alkyl, celluloses such as hydroxypropyl methyl cellulose, hydroxy alkyl celluloses such as hydroxy propyl cellulose, natural or synthetic gums such as guar gum, xanthum gum, and alginates, as well as, ethyl cellulose, polyvinyl pyrrolidone, fats, waxes, polycarboxylic acids or esters such as the Carbopol® (Noveon IP Holdings, Corporation) series of polymers, methacrylic acid copolymers, and methacrylate polymers.

Methods of making matrix dosages are well known in the art and any known method of making such dosages which yields the desired immediate release and controlled release dissolution profiles can be used. One such method involves the mixture of the levodopa and carbidopa combination with a solid polymeric material and one or more pharmaceutically acceptable excipients which are then blended and compressed in controlled release tablet cores. Such tablet cores can be used for further processing as bi-layer tablets, press coated tablets, or film coated tablets.

A coating containing the immediate release carbidopa or carbidopa and levodopa in combination can be added to the outside of the controlled release tablet cores to produce a final dosage form. Such a coating can be prepared by mixing carbidopa alone, or a combination of levodopa and carbidopa, with polyvinylpyrrolidone (PVP) 29/32 or hydroxypropyl methylcellulose (HPMC) and water/isopropyl alcohol and triethyl acetate. Such an immediate release coating can be spray coated onto the tablet cores. The immediate release coating may also be applied using a press-coating process with a blend consisting of 80% by weight levodopa and carbidopa and 20% by weight of lactose and hydroxypropyl methylcellulose type 2910. Press coating techniques are known in the art and are described in U.S. Pat. No. 6,372,254 to Ting et al., incorporated herein by reference in its entirety.

In addition, the formulation of respective release components can occur by appropriate granulation methods as is well known in the art. In wet granulation, solutions of the binding agent (polymer) are added with stirring to the mixed powders. The powder mass is wetted with the binding solution until the mass has the consistency of damp snow or brown sugar. The wet granulated material is forced through a sieving device. Moist material from the milling step is dried by placing it in a temperature controlled container. After drying, the granulated material is reduced in particle size by passing it through a sieving device. Lubricant is added, and the final blend is then compressed into a matrix dosage form.

In fluid-bed granulation, particles of inert material and/or active agent are suspended in a vertical column with a rising air stream. While the particles are suspended, a common granulating material in solution is sprayed into the column. There is a gradual particle buildup under a controlled set of conditions resulting in tablet granulation. Following drying and the addition of lubricant, the granulated material is ready for compression.

In dry-granulation, the active agent, binder, diluent, and lubricant are blended and compressed into tablets. The compressed large tablets are comminuted through the desirable mesh screen by sieving equipment. Additional lubricant is added to the granulated material and blended gently. The material is then compressed into tablets.

Particle Based Dosage Forms

Immediate Release Particles

The immediate release/controlled release dosage forms of the present invention can also take the form of pharmaceutical particles. The dosage forms can include immediate release particles in combination with controlled release particles in a ratio sufficient to deliver the desired dosages of active agents. The controlled release particles can be produced by coating the immediate release particles.

The particles can be produced according to any of a number of well known methods for making particles. The immediate release particles comprise the active agent combination and a disintegrant. Suitable disintegrants include, for example, starch, low-substitution hydroxypropyl cellulose, croscarmellose sodium, calcium carboxymethyl cellulose, hydroxypropyl starch, and microcrystalline cellulose.

In addition to the above-mentioned ingredients, a controlled release matrix may also contain suitable quantities of other materials, for example, diluents, lubricants, binders, granulating aids, colorants, flavorants, and glidants that are conventional in the pharmaceutical arts. The quantities of these additional materials are sufficient to provide the desired effect to the desired formulation. A controlled release matrix incorporating particles may also contain suitable quantities of these other materials such as diluents, lubricants, binders, granulating aids, colorants, flavorants, and glidants that are conventional in the pharmaceutical arts in amounts up to about 75% by weight of the particulate, if desired.

Particles can assume any standard structure known in the pharmaceutical arts. Such structures include, for example, matrix particles, non-pareil cores having a drug layer and active or inactive cores having multiple layers thereon. A controlled release coating can be added to any of these structures to create a controlled release particle.

The term particle as used herein means a granule having a diameter of between about 0.01 mm and about 5.0 mm, preferably between about 0.1 mm and about 2.5 mm, and more preferably between about 0.5 mm and about 2 mm. The skilled artisan will appreciate that particles according to the present invention can be any geometrical shape within this size range and so long as the mean for a statistical distribution of particles falls within the particle sizes enumerated above, they will be considered to fall within the contemplated scope of the present invention.

The release of the therapeutically active agent from the controlled release formulation of the present invention can be further influenced, i.e., adjusted to a desired rate, by the addition of one of more release-modifying agents. The release-modifying agent may be organic or inorganic and include materials that can be dissolved, extracted, or leached from the coating in the environment of use. The pore-formers may comprise one or more hydrophilic materials such as hydroxypropyl methylcellulose. The release-modifying agent may also comprise a semi-permeable polymer. In certain preferred embodiments, the release-modifying agent is selected from hydroxypropyl methylcellulose, lactose, metal stearates, and mixtures thereof.

In one preferred embodiment, oral dosage forms are prepared to include an effective amount of particles as described above within a capsule. For example, melt-extruded particles may be placed in a gelatin capsule in an amount sufficient to provide an effective controlled release dose when ingested and contacted by gastric fluid. In another preferred embodiment, a suitable amount of the particles are compressed into an oral tablet using conventional tableting equipment using standard techniques. Techniques and compositions for making tablets (compressed and molded), capsules (hard and soft gelatin), and pills are also described in *Remington's Pharmaceutical Sciences*, Arthur Osol, editor, pp. 1553–1593 (1980), incorporated herein by reference. The particles can be made by mixing the relevant ingredients and granulating the mixture. The resulting particles are dried and screened, and the particles having the desired size are used for drug formulation.

Controlled Release Particles

The controlled release particles of the present invention slowly release the combination of levodopa and carbidopa when ingested and exposed to gastric fluids, and then to intestinal fluids. The controlled release profile of the formulations of the invention can be altered, for example, by increasing or decreasing the thickness of the retardant coating, i.e., by varying the amount of overcoating. The resultant solid controlled release particles may thereafter be placed in a gelatin capsule in an amount sufficient to provide an effective controlled release dose when ingested and contacted by an environmental fluid, e.g., gastric fluid, intestinal fluid or dissolution media. The particles may be overcoated with an aqueous dispersion of a hydrophobic or hydrophilic material to modify the release profile. The aqueous dispersion of hydrophobic material preferably further includes an effective amount of plasticizer, e.g. triethyl citrate. Preformulated aqueous dispersions of ethylcellulose, such as Aquacoat® (FMC Corporation) or Surelease®(Colorcon, Inc., West Point, Pa., U.S.A), may be used. If Surelease® (Colorcon, Inc., West Point Pa., U.S.A.) is used, it is not necessary to separately add a plasticizer.

The hydrophobic material may be selected from the group consisting of alkylcellulose, acrylic and methacrylic acid polymers and copolymers, shellac, zein, hydrogenated castor oil, hydrogenated vegetable oil, or mixtures thereof. In certain preferred embodiments, the hydrophobic material is a pharmaceutically acceptable acrylic polymer, including but not limited to acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly(methacrylic acid), methacrylicacid alkylamine copolymer, poly(methyl methacrylate), poly(methacrylic acid anhydride), polymethacrylate, polyacrylamide, poly(methacrylic acid anhydride), and glycidyl methacrylate copolymers. In alternate embodiments, the hydrophobic material is selected from materials such as one or more hydroxyalkyl celluloses such as hydroxypropyl methycellulose. The hydroxyalkyl cellulose is preferably a hydroxy ($C_1$ to $C_6$) alkyl cellulose, such as hydroxypropylcellulose, hydroxypropylmethylcellulose, or preferably hydroxyethylcellulose. The amount of the hydroxyalkyl cellulose in the present oral dosage form is determined, inter alia, by the precise rate of active agents desired and may vary from about 1% to about 80%.

In embodiments of the present invention where the coating comprises an aqueous dispersion of a hydrophobic polymer, the inclusion of an effective amount of a plasticizer in the aqueous dispersion of hydrophobic polymer can further improve the physical properties of the film. For example, because ethylcellulose has a relatively high glass transition temperature and does not form flexible films under normal coating conditions, it is necessary to plasticize the ethylcellulose before using it as a coating material. Generally, the amount of plasticizer included in a coating solution is based on the concentration of the film-former, e.g., most often from about 1 percent to about 50 percent by weight of the film-former. Concentration of the plasticizer, however, is preferably determined after careful experimentation with the particular coating solution and method of application.

Examples of suitable plasticizers for ethylcellulose include water-insoluble plasticizers such as dibutyl sebacate, diethyl phthalate, triethyl citrate, tributyl citrate, and triacetin, although other water-insoluble plasticizers (such as acetylated monoglycerides, phthalate esters, castor oil, etc.) may be used. Triethyl citrate is an especially preferred plasticizer for the aqueous dispersions of ethyl cellulose of the present invention.

Examples of suitable plasticizers for the acrylic polymers of the present invention include, but are not limited to, citric acid esters such as triethyl citrate NF XVI, tributyl citrate, dibutyl phthalate, and possibly 1,2-propylene glycol. Other plasticizers which have proved to be suitable for enhancing the elasticity of the films formed from acrylic films such as Eudragit® RL/RS (Rohm Pharma) lacquer solutions include polyethylene glycols, propylene glycol, diethyl phthalate, castor oil, and triacetin. Triethyl citrate is an especially preferred plasticizer for aqueous dispersions of ethyl cellulose. It has further been found that addition of a small amount of talc reduces the tendency of the aqueous dispersion to stick during processing and acts a polishing agent.

One commercially available aqueous dispersion of ethylcellulose is Aquacoat® (FMC Corporation) which is prepared by dissolving the ethylcellulose in a water-immiscible organic solvent and then emulsifying the ethylcellulose in water in the presence of a surfactant and a stabilizer. After homogenization to generate submicron droplets, the organic solvent is evaporated under vacuum to form a pseudolatex. The plasticizer is not incorporated into the pseudolatex during the manufacturing phase. Thus, prior to using the pseudolatex as a coating, the Aquacoat® is mixed with a suitable plasticizer.

Another aqueous dispersion of ethylcellulose is commercially available as Surelease® (Colorcon, Inc., West Point, Pa., U.S.A.). This product is prepared by incorporating plasticizer into the dispersion during the manufacturing process. A hot melt of a polymer, plasticizer (dibutyl sebacate), and stabilizer (oleic acid) is prepared as a homogeneous mixture which is then diluted with an alkaline solution to obtain an aqueous dispersion which can be applied directly onto substrates.

In one preferred embodiment, the acrylic coating is an acrylic resin lacquer used in the form of an aqueous dispersion, such as that which is commercially available from Rohm Pharma under the trade name Eudragit®. In additional preferred embodiments, the acrylic coating comprises a mixture of two acrylic resin lacquers commercially available from Rohm Pharma under the trade names Eudragit® RL 30 D and Eudragit® RS 30 D. Eudragit® RL 30 D and Eudragit® RS 30 are copolymers of acrylic and methacrylic esters with a low content of quaternary ammonium groups, the molar ratio of ammonium groups to the remaining neutral (meth)acrylic esters being 1:20 in Eudragit® RL 30 and 1:40 in Eudragit® RS 30 D. The mean molecular weight is about 150,000 Daltons. The code designations RL (high permeability) and RS (low permeability) refer to the permeability properties of these agents. Eudragit® RL/RS (Rohm Pharma) mixtures are insoluble in water and in digestive fluids, however, coatings formed from them are swellable and permeable in aqueous solutions and digestive fluids.

The Eudragit® RL/RS dispersions may be mixed together in any desired ratio in order to ultimately obtain a controlled-release formulation having a desirable dissolution profile. Desirable controlled-release formulations may be obtained, for instance, from a retardant coating derived from one of a variety of coating combinations, such as 100% Eudragit® RL; 50% Eudragit® RL and 50% Eudragit® RS; or 10% Eudragit® RL and Eudragit® 90% RS. Of course, one skilled in the art will recognize that other acrylic polymers may also be used, for example, Eudragit®L. In addition to modifying the dissolution profile by altering the relative amounts of different acrylic resin lacquers, the dissolution profile of the ultimate product may also be modified, for example, by increasing or decreasing the thickness of the retardant coating.

In preferred embodiments of the present invention, the stabilized product is obtained by subjecting the coated substrate to oven curing at a temperature above the Tg of the plasticized acrylic polymer for the required time period, the optimum values for temperature and time for the particular formulation being determined experimentally. In certain embodiments of the present invention, the stabilized product is obtained via an oven curing conducted at a temperature of about 45° C. for a time period from about 1 to about 48 hours. It is also contemplated that certain products coated with the controlled-release coating of the present invention may require a curing time longer than 24 to 48 hours, e.g., from about 48 to about 60 hours or more.

The coating solutions preferably contain, in addition to the film-former, plasticizer, and solvent system (i.e., water), a colorant to provide elegance and product distinction. Color may be added to the solution of the therapeutically active agent instead of, or in addition to the aqueous dispersion of hydrophobic material. For example, color may be added to Aquacoat® (FMC Corporation) via the use of alcohol or propylene glycol based color dispersions, milled aluminum lakes and opacifiers such as titanium dioxide by adding color with shear to the water soluble polymer solution and then using low shear to the plasticized Aquacoat® (FMC Corporation). Alternatively, any suitable method of providing color to the formulations of the present invention may be used. Suitable ingredients for providing color to the formulation when an aqueous dispersion of an acrylic polymer is used include titanium dioxide and color pigments, such as iron oxide pigments. The incorporation of pigments, may, however, increase the retardant effect of the coating.

Spheroids or beads coated with the therapeutically active agents can be prepared, for example, by dissolving the therapeutically active agents in water and then spraying the solution onto a substrate, for example, non pareil 18/20 beads, using a Wuster insert. Optionally, additional ingredients are also added prior to coating the beads in order to assist the binding of the active agents to the beads, and/or to color the solution, etc. For example, a product which includes hydroxypropyl methylcellulose with or without colorant (e.g., Opadry®, commercially available from Colorcon, Inc.) may be added to the solution and the solution mixed (e.g., for about 1 hour) prior to application onto the beads. The resultant coated substrate, beads in this example, may then be optionally overcoated with a barrier agent to separate the therapeutically active agent from the hydrophobic controlled release coating. An example of a suitable barrier agent is one which comprises hydroxypropylmethylcellulose. However, any film-former known in the art may be used. It is preferred that the barrier agent does not affect the dissolution rate of the final product.

Immediate release particles according to the present invention may be coated with a controlled release coating in order to change the release rate to obtain the dissolution rates according to the present invention.

Press Coated, Pulsatile Dosage Form

In another embodiment of the present invention, the carbidopa and levodopa combination is administered via a press coated pulsatile drug delivery system suitable for oral administration with a controlled release component, which contains a compressed blend of an active agent and one or more polymers, substantially enveloped by an immediate release component, which contains a compressed blend of the active agent and hydrophilic and hydrophobic polymers. The immediate-release component preferably comprises a compressed blend of active agent and one or more polymers with disintegration characteristics such that the polymers disintegrate rapidly upon exposure to the aqueous medium.

The controlled-release component preferably comprises a combination of hydrophilic and hydrophobic polymers. In this embodiment, once administered, the hydrophilic polymer dissolves away to weaken the structure of the controlled-release component, and the hydrophobic polymer retards the water penetration and helps to maintain the shape of the drug delivery system.

In accordance with the present invention, the term "polymer" includes single or multiple polymeric substances, which can swell, gel, degrade or erode on contact with an aqueous environment (e.g., water). Examples include alginic acid, carboxymethylcellulose calcium, carboxymethylcellulose sodium, colloidal silicon dioxide, croscarmellose sodium, crospovidone, guar gum, magnesium aluminum silicate, methylcellulose, microcrystalline cellulose, polacrilin potassium, powdered cellulose, pregelatinized starch, sodium alginate, sodium starch glycolate, starch, ethylcellulose, gelatin, hydroxyethyl cellulose, hydroxypropyl cellulose, hydroxypropyl methylcellulose, polymethacrylates, povidone, pregelatinized starch, shellac, and zein, and combinations thereof.

The term "hydrophilic polymers" as used herein includes one or more of carboxymethylcellulose, natural gums such as guar gum or gum acacia, gum tragacanth, or gum xanthan, hydroxyethyl cellulose, hydroxypropyl cellulose, hydroxypropyl methylcellulose, methylcellulose, and povidone, of which hydroxypropyl methylcellulose is further preferred. The term "hydrophilic polymers" can also include sodium carboxymethycellulose, hydroxymethyl cellulose, polyethelene oxide, hydroxyethyl methyl cellulose, carboxypolymethylene, polyethelene glycol, alginic acid, gelatin, polyvinyl alcohol, polyvinylpyrrolidones, polyacrylamides, polymethacrylamides, polyphosphazines, polyoxazolidines, poly(hydroxyalkylcarboxylic acids), an alkali metal or alkaline earth metal, carageenate alginates, ammonium alginate, sodium alganate, or mixtures thereof.

The hydrophobic polymer of the drug delivery system can be any hydrophobic polymer which will achieve the goals of the present invention including, but not limited to, one or more polymers selected from carbomer, carnauba wax, ethylcellulose, glyceryl palmitostearate, hydrogenated castor oil, hydrogenated vegetable oil type 1, microcrystalline wax, polacrilin potassium, polymethacrylates, or stearic acid, of which hydrogenated vegetable oil type 1 is preferred. Hydrophobic polymers can include, for example, a pharmaceutically acceptable acrylic polymer, including, but not limited to, acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolymer, poly(methyl methacrylate), poly(methyl methacrylate) copolymer, polyacrylamide, aminoalkyl methacrylate copolymer, poly (methacrylic acid anhydride), and glycidyl methacrylate copolymers. Additionally, the acrylic polymers may be cationic, anionic, or non-ionic polymers and may be acrylates, methacrylates, formed of methacrylic acid or methacrylic acid esters. The polymers may also be pH dependent.

The present invention also provides a method for preparing a press coated, pulsatile drug delivery system suitable for oral administration. This method includes the steps of combining an effective amount of an active agent, or a pharmaceutically acceptable salt thereof, and a polymer to form an immediate-release component; combining an effective amount of an active agent, or a pharmaceutically acceptable salt thereof, and a combination of hydrophilic and hydrophobic polymers to form an controlled-release component; and press coating the controlled-release component to substantially envelop the immediate-release component.

A preferred embodiment further includes the steps of combining an effective amount of an active agent, or a pharmaceutically acceptable salt thereof, and a polymer to form an immediate-release component, and press coating the immediate-release component to substantially envelop the controlled-release component. In another preferred embodiment, the combining steps can be done by blending, wet granulation, fluid-bed granulation, or dry granulation according to methods recognized in the art.

The term "substantially envelop" is intended to define the total or near-total enclosure of a component. Such an enclosure includes, preferably, at least 80% enclosure, more preferably at least 90% enclosure, and most preferably at least 99% enclosure.

The following examples describe and illustrate the processes and products of the present invention. These examples are intended to be merely illustrative of the present invention, and not limiting thereof in either scope or spirit. Those skilled in the art will readily understand that variations of the materials, conditions, and processes described in these examples can be used. All references cited herein are incorporated by reference.

EXAMPLE 1

The method described below was employed to obtain a press coated, pulsatile drug delivery system, the composition of which is set forth in Tables 1 and 2.

Appropriate weights of levodopa and carbidopa (weights shown in Tables 1 and 2) are intimately mixed for use in preparing immediate release and controlled release components of the formulations of the present invention.

Immediate-Release Component

The active agents are first mixed with silicon dioxide in a Patterson-Kelley V-blender for 10 minutes. Then microcrystalline cellulose and croscarmellose sodium are added and blended for 10 more minutes. Finally, magnesium stearate is added to the blender and mixed for another 10 minutes. The powder blend is then compressed using a Manesty Dry-cota with a 0.2031 inch diameter, round, flat-face punch and die set. The hardness of the tablets is maintained at 4±2 kp.

Immediate-Release Component Plus Controlled-Release Component

The active agents are first mixed with silicon dioxide in a Patterson-Kelley V-blender for 10 minutes. Then hydroxypropyl methylcellulose 2208 and microcrystalline cellulose are added and blended for 10 more minutes. Finally, hydrogenated vegetable oil and magnesium stearate are added to the blender and mixed for another 10 minutes. The core tablets are press-coated using the Manesty Dry-cota with 0.3600" in diameter, round, shallow concave punch and die set. The hardness of the tablets is maintained at 12±4 kp.

EXAMPLE 2

Immediate-Release Component Plus Controlled-Release Component Plus Immediate-Release Component The method of manufacture for the controlled-release tablets is the same as described in Example 1. The application of the immediate-release component was done by charging the controlled-release tablets into a perforated pan coater or a fluidized particle coater and coating the tablet cores with a solution consisting of levodopa and carbidopa 80% w/lactose and hydroxypropyl methylcellulose type 2910.

TABLE 1

| | Quantity/Tablet | |
|---|---|---|
| | Example #1 RT-010 (press-coated w/o immediate-release coating) | Example #2 RT-011 (press coated w/ immediate-release coating) |
| Immediate-Release (IR) Component | | |
| Levodopa/carbidopa 4:1 ratio 80% w/lactose | 50.0 mg | 50.0 mg |
| Croscarmellose sodium | 1.6 mg | 1.6 mg |
| Microcrystalline cellulose | 26.8 mg | 26.8 mg |
| Colloidal silicon dioxide | 0.8 mg | 0.8 mg |
| Magnesium stearate | 0.8 mg | 0.8 mg |
| Total: | 80.0 mg | 80.0 mg |
| IR Component Plus Controlled-Release (CR) Component | | |
| IR Component | 80.0 mg | 80.0 mg |
| Levodopa/carbidopa 4:1 ratio 80% w/lactose | 37.5 mg | 18.8 mg |
| Hydroxypropyl methylcellulose type 2208 | 61.6 mg | 61.6 mg |
| Microcrystalline cellulose | 70.3 mg | 89.0 mg |
| Hydrogenated vegetable oil type 1 | 46.2 mg | 46.2 mg |
| Colloidal silicon dioxide | 2.2 mg | 2.2 mg |
| Magnesium stearate | 2.2 mg | 2.2 mg |
| Total: | 300.0 mg | 300.00 mg |
| IR Component Plus CR Component Plus Immediate-Release Component | | |
| IR Component Plus ER Component | | 300.0 mg |
| Levodopa/carbidopa 4:1 ratio 80% w/lactose | | 18.7 mg |
| Hydroxypropyl methylcellulose type 2910 | | 1.9 mg |
| Total: | | 320.6 mg |

TABLE 2

EXCIPIENT RANGE

| | Quantity/tablet Example #1 RT-010 (press coated w/o IR coating) | Percent | Range |
|---|---|---|---|
| Immediate-Release Component | | | |
| Levodopa/carbidopa 4:1 ratio 80% w/lactose | 50.0 mg | 62.5% | |
| Croscarmellose sodium | 1.6 mg | 2.0% | 0.5–10.0% |
| Microcrystalline cellulose | 26.8 mg | 33.5% | 18.0–36.0% |
| Colloidal silicon dioxide | 0.8 mg | 1.0% | 0.5–2.0% |
| Magnesium stearate | 0.8 mg | 1.0% | 0.5–2.0% |
| Total: | 80.0 mg | | |
| Controlled-Release Component | | | |
| Levodopa/carbidopa 4:1 ratio 80% w/lactose | 37.5 mg | 17.0% | |
| Hydroxypropyl methylcellulose type 2208 | 61.6 mg | 28.0% | 15.0–40.0% |
| Microcrystalline cellulose | 70.3 mg | 32.0% | 8.0–57.0% |
| Hydrogenated vegetable oil type 1 | 46.2 mg | 21.0% | 10.0–30.0% |
| Colloidal silicon dioxide | 2.2 mg | 1.0% | 0.5–2.0% |
| Magnesium stearate | 2.2 mg | 1.0% | 0.5–2.0% |
| Total: | 220.0 mg | | |

EXAMPLE 3

Example 3 employs the ingredients and amounts listed in Tables 3A, 3B, and 3C below for the formulations PX00502, PX03002, and PX03102, respectively.

For each batch, whether 502, 3002 or 3102, the following procedure is used: All ingredients, except magnesium stearate are weighed and mixed thoroughly. The mixed ingredients are added to a high shear granulator and mixed for 5 minutes, with an impeller speed of 5 and a chopper speed of 4. Deionized water is employed as the granulating agent. Granules so made are dried in an oven overnight and then screened through a #20 mesh (US standard). Oversize granules are milled, screened with the process repeated until all particles can be screened through a #20 mesh. The magnesium stearate is added to the screened particles and mixed thoroughly.

The resulting mixture can then be used for different types of dosage forms as set out in examples 4 and 5.

TABLE 3A

| | per tablet | |
|---|---|---|
| PX00502 | (w/w) % | amount in mg |
| Carbidopa | 18 | 53.8 |
| Levodopa | 67 | 200.1 |
| Klucel | 12.9 | 38.5 |
| Lake blend | 0.3 | 0.9 |
| Mg stearate | 1.8 | 5.4 |
| Total | 100 | 298.7 |

TABLE 3B

| | per tablet | |
|---|---|---|
| PX03002 | (w/w) % | amount in mg |
| Carbidopa | 11.3 | 27 |
| Levodopa | 41.9 | 100 |

TABLE 3B-continued

| PX03002 | (w/w) % | per tablet amount in mg |
|---|---|---|
| Avicel | 33.2 | 79.2 |
| Starch | 11.1 | 26.5 |
| Acdisol | 0.8 | 1.9 |
| Mg stearate | 1.7 | 3.8 |
| Total | 100 | 238.4 |

TABLE 3C

| PX03102 | (w/w) % | per tablet amount in mg |
|---|---|---|
| Carbidopa | 9.3 | 26.9 |
| Levodopa | 34.6 | 100.1 |
| Avicel | 27.4 | 79.3 |
| Starch | 27.4 | 79.3 |
| Mg Stearate | 1.3 | 3.8 |
| Total | 100 | 289.4 |

FIG. 1 shows the dissolution profiles of profiles of carbidopa/levodopa immediate release (IR) 25/100 mg formulations PX03002 and PX03102. As discussed above, all dissolution profiles were carried out by the standard USP paddle method of 50 rpm in 900 ml aqueous buffer at pH 4 at 37° C.

Figure 2:
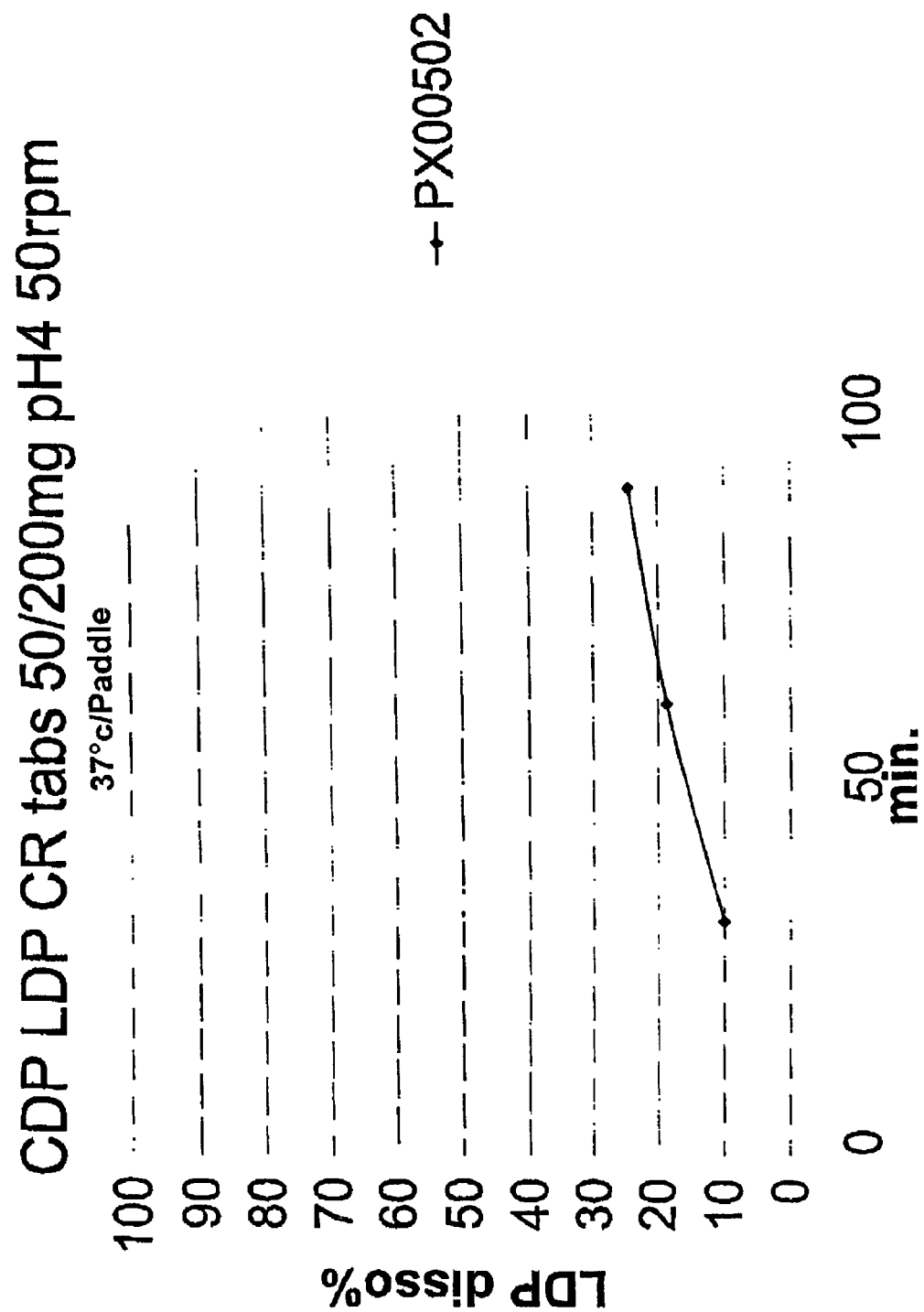
FIG. 2 is a graph of the dissolution profile of a carbidopa/levodopa controlled release (CR) 50/200 mg formulation PX00502 according to measurements under the USP paddle method of 50 rpm in 900 ml acetate buffer at pH 4 at 37° C.

FIG. 2 shows the dissolution profile of a carbidopa/levodopa controlled release (CR) 50/200 mg formulation PX00502.

Figure 3:
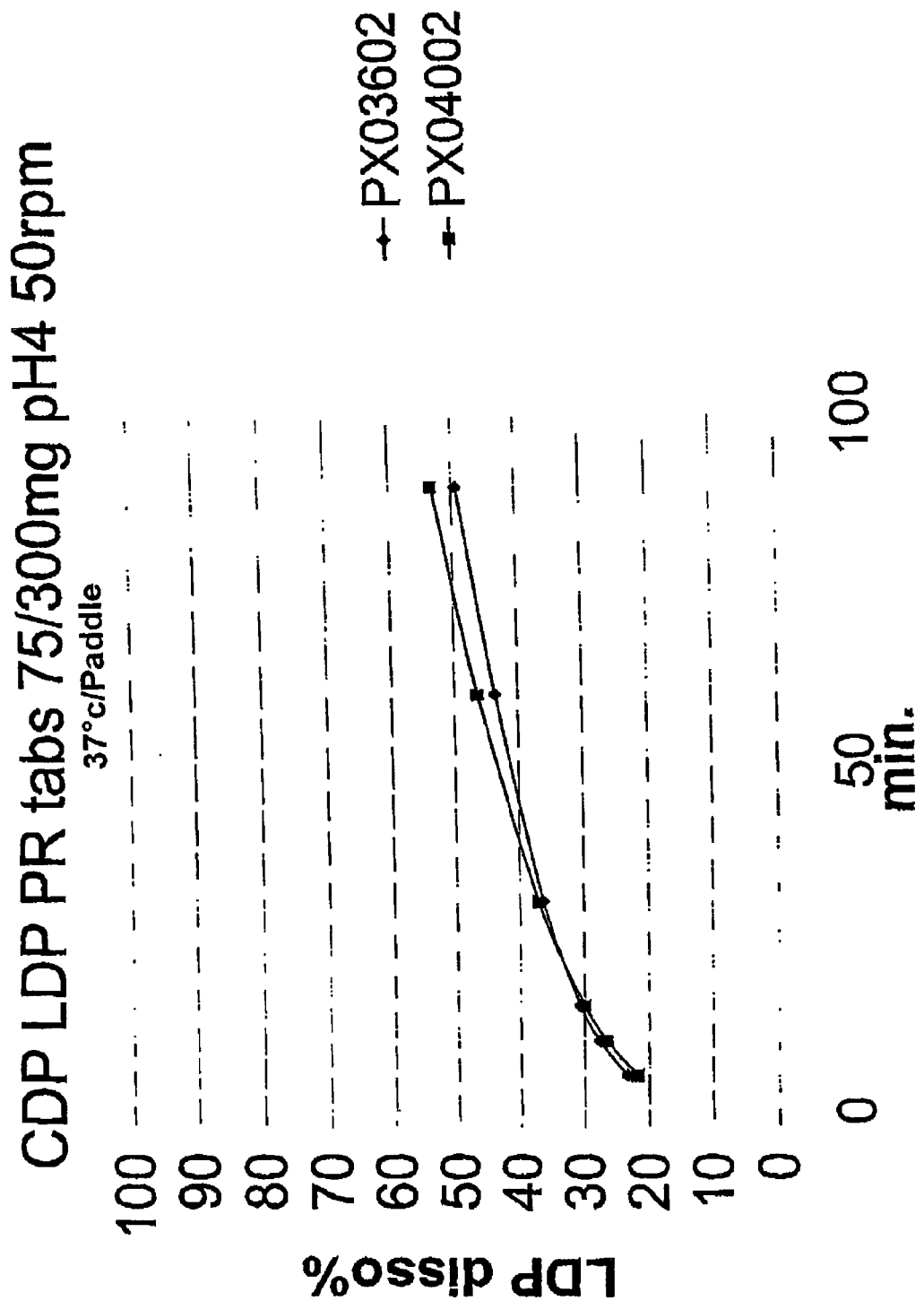
FIG. 3 is a graph of the dissolution profiles of carbidopa/levodopa 75/300 mg formulations PX03602 and PX04002 according to measurements under the USP paddle method of 50 rpm in 900 ml acetate buffer at pH 4 at 37° C.

FIG. 3 shows the dissolution profiles of carbidopa/levodopa 75/300 mg formulations PX03602 and PX04002. Note that controlled release (or prolonged release (PR)) tablets PX03602 comprise the combination of PX0502(CR) and PX03102, and PR tablets PX04002 comprise the combination of PX0502(CR) and PX03002.

EXAMPLE 4

The lot 3102 particles produced in Example 3 are segregated into two equal portions of 125 grams each. One portion is coated in a fluidized pan with a mixture of 24.25 g of PVP 29/32, 1000 g of deionized water and isopropyl alcohol (15%), and 0.75 g of triethyl acetate. The particles are dried and thoroughly mixed with the uncoated particles. The particle mixture is then loaded into immediate release gelatin capsules.

EXAMPLE 5

Particles produced according to lots 3002 and 502 of Example 3 are loaded into the two separate hoppers of a dual layer tablet punch. The punch is actuated and two-layer tablets are produced.

EXAMPLE 6

Figure 4:
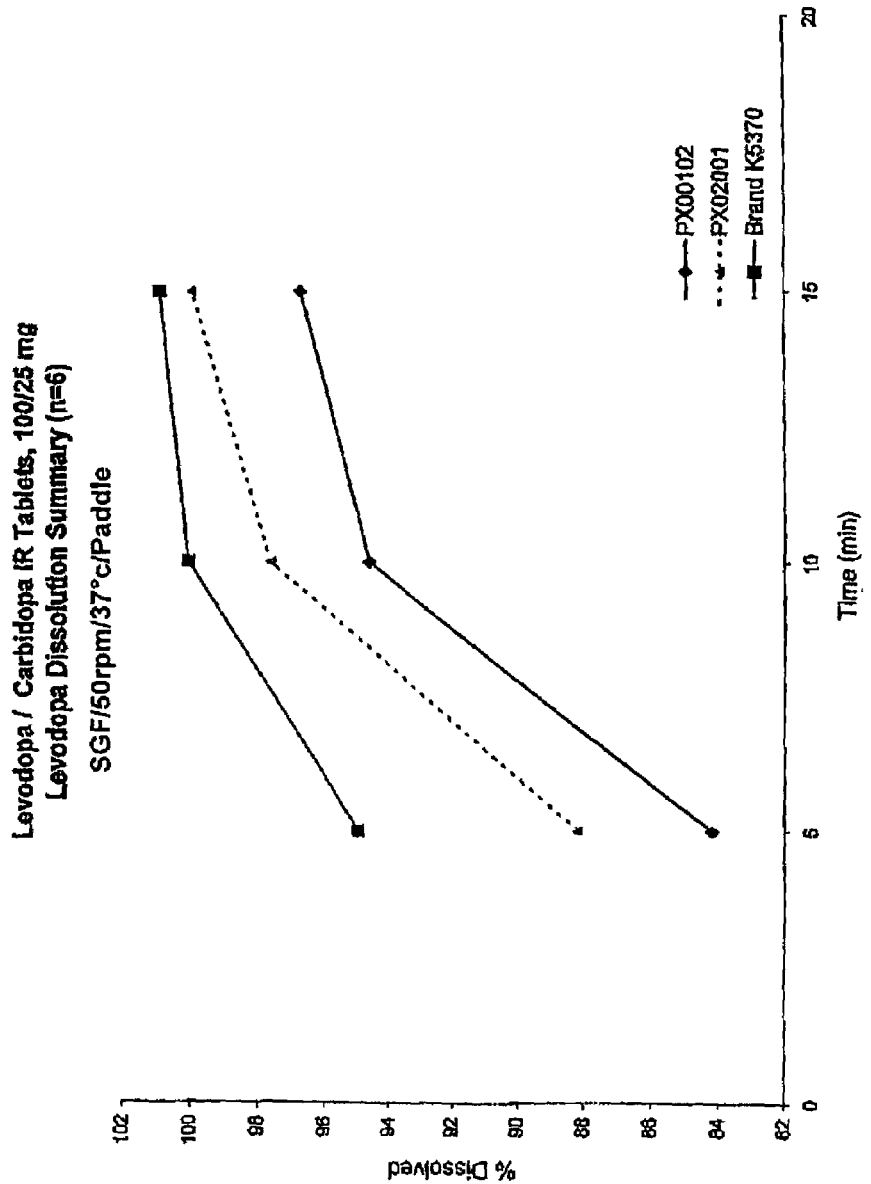
FIG. 4 is a graph of the dissolution profiles of carbidopa/levodopa immediate release (IR) 25/100 mg formulations PX00102, PX02001, and Brand K5370 according to measurements under the USP paddle method of 50 rpm in 900 ml at pH 1.2(0.1 N HCL) at 37° C.

The dissolution summaries for carbidopa/levodopa immediate release (IR) 25/100 mg formulations PX00102, PX02001, and Brand K5370 are shown in Tables 4, 5, and 6, respectively. All data was obtained according to measurements under the USP paddle method of 50 rpm in 900 ml at pH 1.2 (0.1 N HCL) at 37° C. FIG. 4 is a graph of the dissolution profiles of carbidopa/levodopa immediate release (IR) 25/100 mg formulations PX00102, PX02001, and Brand K5370.

EXAMPLE 7

Figure 5:
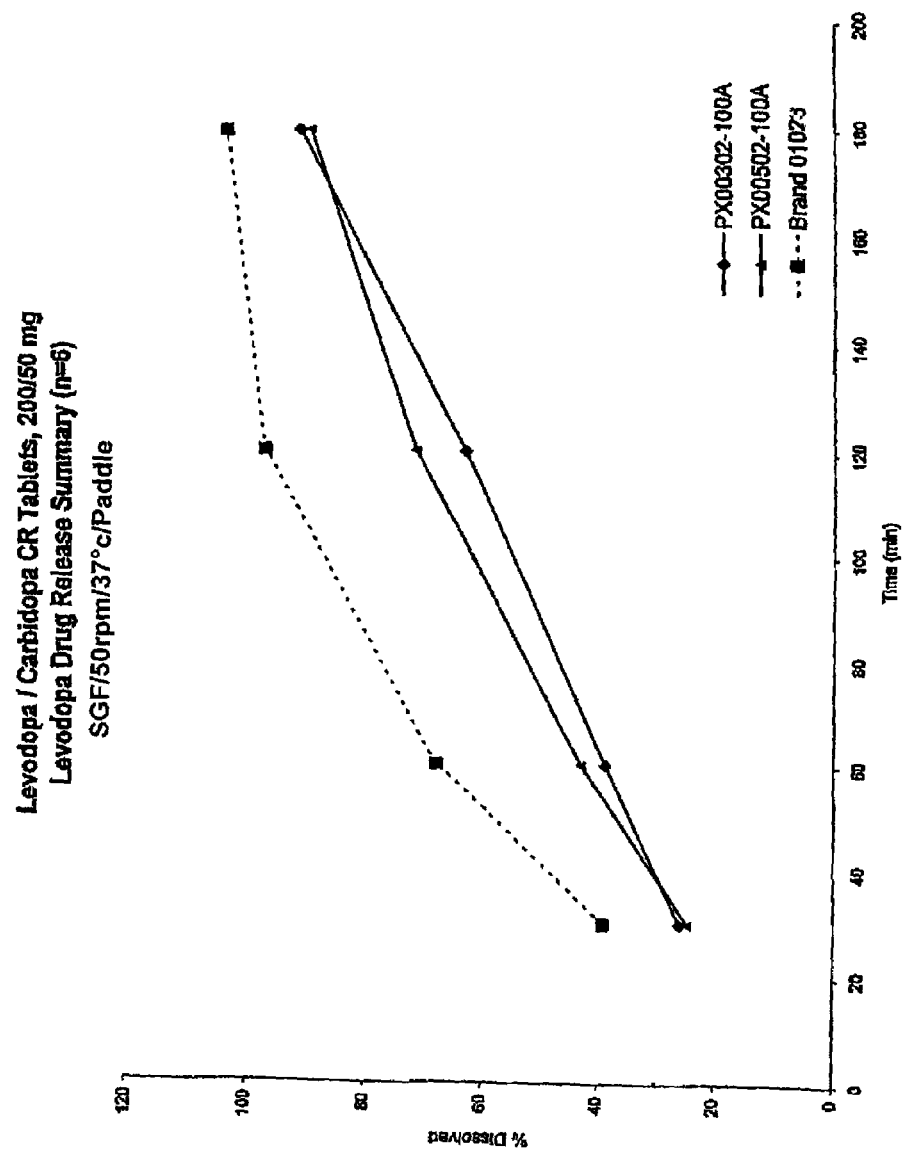
FIG. 5 is a graph of the dissolution profiles of carbidopa/levodopa controlled release (CR) 50/200 mg formulations PX00302, PX00502, and Brand 01023 according to measurements under the USP paddle method of 50 rpm in 900 ml at pH 1.2(0.1 N HCL) at 37° C.

The dissolution summaries for carbidopa/levodopa controlled release (CR) 50/200 mg formulations PX00302, PX00502, and Brand 01023 are shown in Tables 7, 8, and 9, respectively. All data was obtained according to measurements under the USP paddle method of 50 rpm in 900 ml at pH 1.2 (0.1 N HCL) at 37 C. FIG. 5 is a graph of the dissolution of carbidopa/levodopa controlled release (CR) 50/200 mg formulations PX00302, PX00502, and Brand 01023.

EXAMPLE 8

Figure 6:
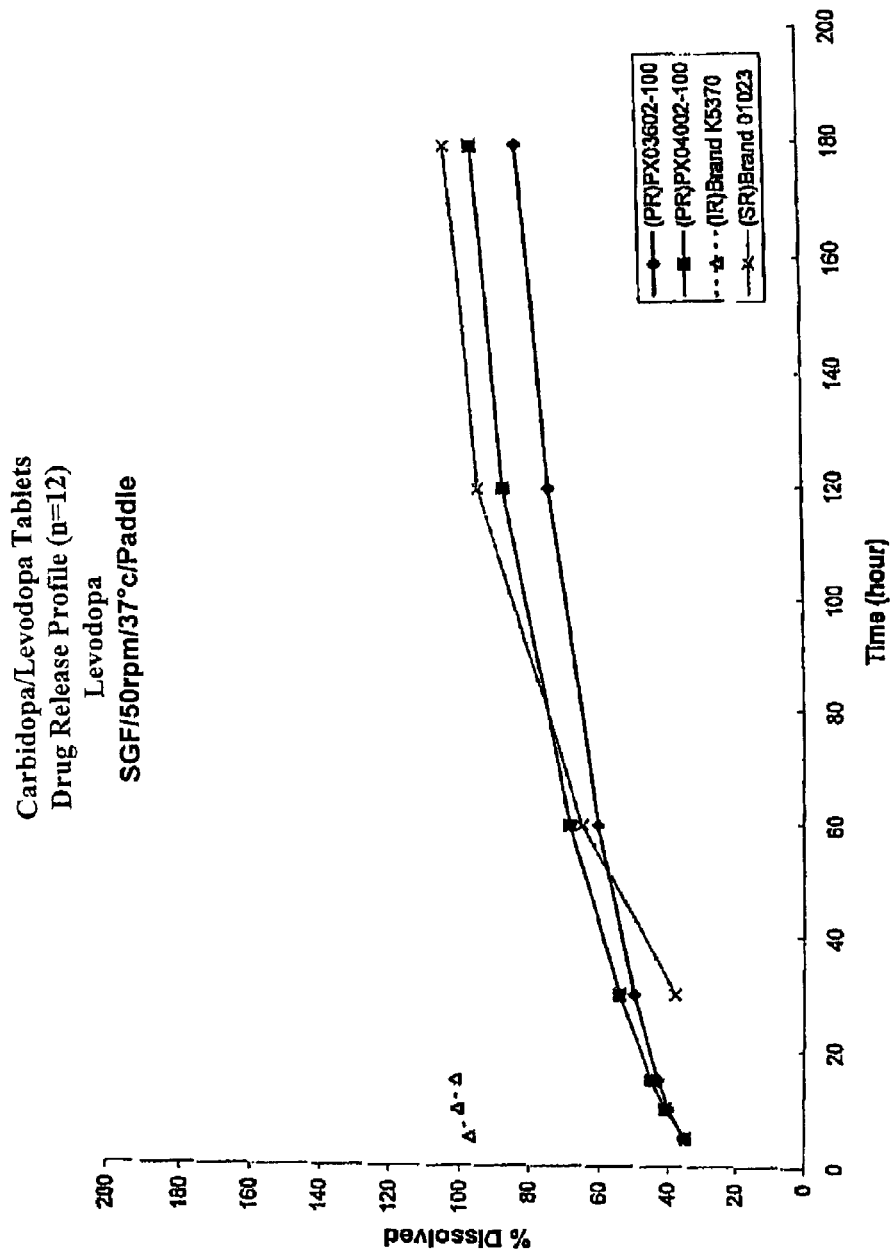
FIG. 6 is a graph of the dissolution profiles of carbidopa/levodopa formulations PX03602 (controlled release, 75/300 mg), PX04002 (controlled release, 75/300 mg), Brand K5370 (immediate release, 25/100 mg), and Brand 01023 (controlled release, 50/200 mg) according to measurements under the USP paddle method of 50 rpm in 900 ml at pH 1.2 (0.1 N HCL) at 37° C.

The dissolution summaries for carbidopa/levodopa formulations PX03602 (controlled release, 75/300 mg), PX04002 (controlled release, 75/300 mg), Brand K5370 (immediate release, 25/100 mg), and Brand 01023 (controlled release, 50/200 mg) are shown in Tables 10, 11, 12, and 13, respectively. All data was obtained according to measurements under the USP paddle method of 50 rpm in 900 ml at pH 1.2 (0.1 N HCL) at 37 C. FIG. 6 is a graph of the dissolution profiles of carbidopa/levodopa formulations PX03602 (controlled release, 75/300 mg), PX04002 (controlled release, 75/300 mg), Brand K5370 (immediate release, 25/100 mg), and Brand 01023 (controlled release, 50/200 mg).

As noted in Example 3, controlled release (or prolonged release (PR)) tablets PX03602 comprise the combination of PX0502(CR) and PX03102, and PR tablets PX04002 comprise the combination of PX0502(CR) and PX03002.

Data for FIG. 4

Levodopa/Carbidopa IR Tablets, 100/25 mg

Levodopa Dissolution Summary (n=6)

SGF/37° C./50 rpm/Paddle

TABLE 4

| Lot PX00102-100 T = 0 (Ref: F1386, p. 62–67) | | | | | | | | | | | | | | | | |
|---|---|---|---|---|---|---|---|---|---|---|---|---|---|---|---|---|
| | % Dissolved | | | | | | | | | | | | Range | | | |
| Time (min) | V1 | V2 | V3 | V4 | V5 | V6 | V7 | V8 | V9 | V10 | V11 | V12 | Min | Max | Mean | SD |
| 5 | 88 | 82 | 90 | 83 | 89 | 89 | 85 | 87 | 85 | 85 | 68 | 79 | 68 | 90 | 84 | 6.03 |
| 10 | 96 | 90 | 95 | 91 | 95 | 99 | 94 | 96 | 95 | 99 | 89 | 96 | 89 | 99 | 95 | 3.18 |
| 15 | 98 | 92 | 96 | 93 | 97 | 100 | 96 | 97 | 99 | 101 | 91 | 100 | 91 | 101 | 97 | 3.2 |

TABLE 5

Lot PX02001-100 T = 0 (Ref: F1386, p. 62–67)

| Time (min) | V1 | V2 | V3 | V4 | V5 | V6 | V7 | V8 | V9 | V10 | V11 | V12 | Min | Max | Mean | SD |
|---|---|---|---|---|---|---|---|---|---|---|---|---|---|---|---|---|
| | | | | | | % Dissolved | | | | | | | | Range | | |
| 5 | 87 | 96 | 83 | 95 | 80 | 97 | 87 | 89 | 84 | 82 | 90 | 88 | 80 | 97 | 88 | 5.57 |
| 10 | 98 | 98 | 97 | 101 | 92 | 100 | 98 | 98 | 98 | 93 | 98 | 100 | 92 | 101 | 98 | 2.64 |
| 15 | 100 | 99 | 100 | 103 | 97 | 101 | 100 | 100 | 101 | 97 | 100 | 101 | 97 | 103 | 100 | 1.68 |

TABLE 6

Brand (Sinemet, exp. 02/05) Lot K5370, T = 0 (Ref: F1351, p. 78–82)

| Time (min) | V1 | V2 | V3 | V4 | V5 | V6 | V7 | V8 | V9 | V10 | V11 | V12 | Min | Max | Mean | SD |
|---|---|---|---|---|---|---|---|---|---|---|---|---|---|---|---|---|
| | | | | | | % Dissolved | | | | | | | | Range | | |
| 5 | 92 | 89 | 97 | 97 | 93 | 97 | 94 | 95 | 92 | 99 | 93 | 102 | 89 | 102 | 95 | 3.62 |
| 10 | 99 | 95 | 100 | 100 | 99 | 102 | 101 | 99 | 99 | 101 | 101 | 104 | 95 | 104 | 100 | 2.05 |
| 15 | 100 | 97 | 101 | 101 | 100 | 103 | 102 | 100 | 101 | 101 | 101 | 104 | 97 | 104 | 101 | 1.69 |

Data for FIG. 5

Levodopa/Carbidopa CR Tablets, 200/50 mg

Levodopa Dissolution Summary (n=6)

SGF/37° C./50 rpm/Paddle

TABLE 7

PX00302-100A, T = 0 (Ref: F1351, P. 87–94)

| Time (min) | V1 | V2 | V3 | V4 | V5 | V6 | V7 | V8 | V9 | V10 | V11 | V12 | Min | Max | Mean | SD |
|---|---|---|---|---|---|---|---|---|---|---|---|---|---|---|---|---|
| | | | | | | % Dissolved | | | | | | | | Range | | |
| 30 | 26 | 26 | 28 | 26 | 25 | 25 | 24 | 26 | 26 | 26 | 26 | 26 | 24 | 28 | 26 | 1.07 |
| 60 | 40 | 39 | 41 | 39 | 37 | 39 | 36 | 38 | 39 | 39 | 39 | 39 | 36 | 41 | 39 | 1.21 |
| 120 | 58 | 62 | 74 | 63 | 56 | 66 | 56 | 57 | 70 | 65 | 58 | 65 | 56 | 74 | 62 | 5.87 |
| 180 | 83 | 90 | 101 | 92 | 75 | 97 | 82 | 87 | 98 | 78 | 93 | 100 | 75 | 101 | 90 | 8.82 |

TABLE 8

PX00502-100A, T = 0 (Ref: F1351, P. 87–94)

| Time (min) | V1 | V2 | V3 | V4 | V5 | V6 | V7 | V8 | V9 | V10 | V11 | V12 | Min | Max | Mean | SD |
|---|---|---|---|---|---|---|---|---|---|---|---|---|---|---|---|---|
| | | | | | | % Dissolved | | | | | | | | Range | | |
| 30 | 23 | 24 | 24 | 26 | 25 | 24 | 24 | 25 | 25 | 25 | 24 | 24 | 23 | 26 | 24 | 0.82 |
| 60 | 40 | 43 | 43 | 44 | 45 | 42 | 43 | 44 | 43 | 44 | 42 | 42 | 40 | 45 | 43 | 1.40 |
| 120 | 67 | 71 | 70 | 72 | 75 | 68 | 70 | 73 | 71 | 72 | 69 | 69 | 67 | 75 | 71 | 2.17 |
| 180 | 84 | 88 | 88 | 88 | 91 | 84 | 90 | 93 | 89 | 88 | 86 | 88 | 84 | 93 | 88 | 2.46 |

TABLE 9

Brand 01023, T = 0 (Ref: F1351, P. 83–86)

| Time (min) | V1 | V2 | V3 | V4 | V5 | V6 | V7 | V8 | V9 | V10 | V11 | V12 | Min | Max | Mean | SD |
|---|---|---|---|---|---|---|---|---|---|---|---|---|---|---|---|---|
| | | | | | | % Dissolved | | | | | | | | Range | | |
| 30 | 37 | 47 | 42 | 42 | 42 | 34 | 42 | 41 | 30 | 41 | 37 | 34 | 30 | 47 | 39 | 4.81 |
| 60 | 64 | 79 | 71 | 71 | 74 | 59 | 75 | 69 | 53 | 71 | 66 | 60 | 53 | 79 | 68 | 7.69 |

TABLE 9-continued

Brand 01023, T = 0 (Ref: F1351, P. 83–86)

| Time (min) | V1 | V2 | V3 | V4 | V5 | V6 | V7 | V8 | V9 | V10 | V11 | V12 | Min | Max | Mean | SD |
|---|---|---|---|---|---|---|---|---|---|---|---|---|---|---|---|---|
| | | | | | % Dissolved | | | | | | | | Range | | | |
| 120 | 92 | 101 | 99 | 99 | 99 | 93 | 102 | 98 | 84 | 97 | 97 | 93 | 84 | 102 | 96 | 4.86 |
| 180 | 101 | 103 | 103 | 102 | 102 | 105 | 103 | 101 | 103 | 100 | 102 | 104 | 100 | 105 | 102 | 1.55 |

Data for FIG. 6

Levodopa/Carbidopa Compositions

Drug Release Summary (n=12), SGF/37° C./50 rpm/Paddle

TABLE 10

(PR, 75/300 mg) PX03602-100, (Ref: PP444, p. 81–87)

| Time (min) | V1 | V2 | V3 | V4 | V5 | V6 | V7 | V8 | V9 | V10 | V11 | V12 | Min | Max | Mean | SD |
|---|---|---|---|---|---|---|---|---|---|---|---|---|---|---|---|---|
| | | | | | % Dissolved | | | | | | | | Range | | | |
| 5 | 34.6 | 39.9 | 35.3 | 33.2 | 38.0 | 37.6 | 42.2 | 32.1 | 28.6 | 33.6 | 38.3 | 33.6 | 29 | 42 | 36 | 3.8 |
| 10 | 39.1 | 45.0 | 38.9 | 36.9 | 41.3 | 41.4 | 47.7 | 36.7 | 33.3 | 37.5 | 42.4 | 39.0 | 33 | 48 | 40 | 3.9 |
| 15 | 42.0 | 49.0 | 41.2 | 39.2 | 43.5 | 44.7 | 51.5 | 40.1 | 36.7 | 40.1 | 45.3 | 42.8 | 37 | 52 | 43 | 4.2 |
| 30 | 48.8 | 59.0 | 45.9 | 44.4 | 48.4 | 51.3 | 60.2 | 47.8 | 42.6 | 46.7 | 52.5 | 51.5 | 43 | 60 | 50 | 5.4 |
| 60 | 55.5 | 75.9 | 52.6 | 51.9 | 55.6 | 61.8 | 72.0 | 59.4 | 51.2 | 56.7 | 63.2 | 64.7 | 51 | 76 | 60 | 7.9 |
| 120 | 65.8 | 98.9 | 61.9 | 62.4 | 65.5 | 72.3 | 82.5 | 74.7 | 63.3 | 70.6 | 76.9 | 81.5 | 62 | 99 | 73 | 10.9 |
| 180 | 73.7 | 102.2 | 68.2 | 69.1 | 72.1 | 80.1 | 88.2 | 83.6 | 70.7 | 79.5 | 86.9 | 91.0 | 68 | 102 | 80 | 10.4 |

TABLE 11

(PR, 75/300 mg) PX04002-100, (Ref: TV490, p. 54–64)

| Time (min) | V1 | V2 | V3 | V4 | V5 | V6 | V7 | V8 | V9 | V10 | V11 | V12 | Min | Max | Mean | SD |
|---|---|---|---|---|---|---|---|---|---|---|---|---|---|---|---|---|
| | | | | | % Dissolved | | | | | | | | Range | | | |
| 5 | 35.1 | 34.0 | 27.3 | 29.2 | 30.4 | 24.0 | 33.7 | 33.5 | 36.3 | 33.8 | 36.3 | 35.6 | 24 | 36 | 35 | 1.3 |
| 10 | 40.6 | 38.5 | 32.0 | 33.8 | 37.4 | 29.5 | 39.8 | 38.5 | 42.4 | 41.8 | 40.8 | 41.7 | 30 | 42 | 41 | 1.5 |
| 15 | 44.2 | 41.4 | 35.1 | 36.8 | 42.2 | 32.8 | 43.9 | 41.9 | 46.6 | 46.9 | 44.4 | 46.1 | 33 | 47 | 45 | 1.9 |
| 30 | 52.3 | 47.3 | 41.4 | 43.2 | 52.5 | 39.2 | 52.6 | 49.5 | 56.0 | 57.7 | 53.0 | 55.3 | 39 | 58 | 54 | 2.9 |
| 60 | 64.7 | 56.1 | 51.0 | 52.7 | 66.8 | 48.7 | 64.9 | 61.2 | 70.6 | 75.0 | 66.9 | 69.8 | 49 | 75 | 68 | 4.8 |
| 120 | 79.3 | 68.8 | 64.4 | 71.4 | 84.6 | 63.1 | 80.4 | 78.2 | 89.9 | 92.0 | 84.9 | 88.0 | 63 | 92 | 86 | 5.4 |
| 180 | 87.1 | 77.5 | 73.2 | 75.4 | 93.5 | 72.0 | 89.0 | 88.8 | 96.3 | 96.2 | 93.9 | 94.1 | 72 | 96 | 93 | 3.4 |

TABLE 12

(IR 25/100 mg) Brand Lot K5370 (Ref: BT476, p. 83–91 & BT497, p. 29–35)

| Time | V1 | V2 | V3 | V4 | V5 | V6 | V7 | V8 | V9 | V10 | V11 | V12 | Min | Max | Mean | SD |
|---|---|---|---|---|---|---|---|---|---|---|---|---|---|---|---|---|
| | | | | | % Dissolved | | | | | | | | Range | | | |
| 5 min | 100.8 | 95.9 | 94.6 | 99.1 | 96.5 | 97.1 | 97.6 | 93.0 | 99.2 | 100.8 | 93.7 | 98.8 | 93 | 101 | 97 | 2.6 |
| 10 min | 101.7 | 99.3 | 100.3 | 102.6 | 100.9 | 100.9 | 99.7 | 98.3 | 101.9 | 103.4 | 98.3 | 100.5 | 98 | 103 | 101 | 1.6 |
| 15 min | 101.6 | 100.7 | 100.7 | 103.1 | 101.8 | 101.3 | 100.7 | 100.7 | 102.0 | 103.6 | 99.6 | 100.7 | 100 | 104 | 101 | 1.1 |

TABLE 13

(SR 50/200 mg) Brand Lot 01023 (Ref: PP496, p. 22–29)

| | % Dissovled | | | | | | | | | | | | Range | | | |
|---|---|---|---|---|---|---|---|---|---|---|---|---|---|---|---|---|
| Time (min) | V1 | V2 | V3 | V4 | V5 | V6 | V7 | V8 | V9 | V10 | V11 | V12 | Min | Max | Mean | SD |
| 30 | 45.9 | 41.2 | 36.5 | 39.0 | 36.3 | 35.7 | 40.5 | 36.7 | 36.5 | 42.5 | 30.3 | 30.5 | 30 | 46 | 38 | 4.6 |
| 60 | 77.2 | 72.0 | 62.3 | 65.9 | 61.5 | 60.6 | 69.7 | 61.9 | 62.0 | 74.7 | 53.4 | 54.3 | 53 | 77 | 65 | 7.5 |
| 120 | 98.9 | 98.9 | 91.7 | 94.1 | 89.1 | 88.8 | 95.7 | 90.2 | 89.8 | 103.9 | 85.7 | 85.4 | 85 | 104 | 93 | 5.7 |
| 180 | 101.3 | 103.1 | 101.4 | 100.8 | 99.2 | 98.1 | 99.2 | 99.7 | 99.4 | 104.6 | 101.3 | 99.1 | 98 | 105 | 101 | 1.9 |

What is claimed is:

1. A pharmaceutical dosage form having an immediate release component and a controlled release component comprising:
   a) an immediate release component comprising a ratio of carbidopa to levodopa of from about 1:1 to about 1:50 such that the in vitro dissolution rate of the immediate release component according to measurements under the USP paddle method of 50 rpm in 900 ml aqueous buffer at pH 4 at 37° C. is from about 10% to about 99% levodopa released after 15 minutes and from about 60% to about 99% after 1 hour; and
   b) a controlled release component comprising a ratio of carbidopa to levodopa of from about 1:1 to about 1:50 such that the in vitro dissolution rate of the controlled release component according to measurements under the USP paddle method of 50 rpm in 900 ml aqueous buffer at pH 4 at 37° C. is from about 10% to about 60% levodopa released after 1 hour; from about 20% to about 80% levodopa eased after 2 hours; and from about 30% to about 99% levodopa released after about 6 hours, the in vitro release rate chosen such that the initial peak plasma level of levodopa obtained in vivo occurs between 0.1 and 6 hours after administration of the dosage form to a patient.

2. A pharmaceutical dosage form according to claim 1 wherein said immediate release component comprises a ratio of carbidopa to levodopa of from about 1:1 to about 1:50 such that the in vitro dissolution rate of the immediate release component according to measurements under the USP paddle method of 50 rpm in 900 ml aqueous buffer at ph 4 at 37° C. is from about 10% to about 99% levodopa released after 15 minutes and from about 75% to about 99% after 1 hour; and
   said controlled release component comprises a ratio of carbidopa to levodopa of from about 1:1 to about 1:50 such that the in vitro dissolution rate of the controlled release component according to measurements under the USP paddle method of 50 rpm in 900 ml aqueous buffer at pH 4 at 37° C. is from about 10% to about 60% levodopa released after 1 hour; from about 25% to about 80% levodopa released after 2 hours; from about 30% to about 85% levodopa released after 4 hours; and from about 40% to about 99% levodopa released after about 6 hours, the in vitro release rate chosen such that the initial peak plasma level of levodopa obtained in vivo occurs between 0.1 and 6 hours after administration of the dosage form to a patient.

3. A pharmaceutical dosage form according to claim 2 wherein the immediate release component comprises a ratio of carbidopa to levodopa of from about 1:1 to about 1:10.

4. A pharmaceutical dosage form according to claim 2 wherein the immediate release component comprises a ratio of carbidopa to levodopa of from about 1:1 to about 1:5.

5. A pharmaceutical dosage form according to claim 2 wherein the immediate release component comprises a ratio of carbidopa to levodopa of from about 1:1 to about 1:4.

6. A pharmaceutical dosage form according to claim 2 wherein the controlled release component comprises a ratio of carbidopa to levodopa of from about 1:1 to about 1:10.

7. A pharmaceutical dosage form according to claim 2 wherein the controlled release component comprises a ratio of carbidopa to levodopa of from about 1:1 to about 1:5.

8. A pharmaceutical dosage form according to claim 2 wherein the controlled release component comprises a ratio of carbidopa to levodopa of from about 1:1 to about 1:4.

9. A pharmaceutical dosage form according to claim 2 wherein the in vitro dissolution rate of carbidopa of the immediate release component according to measurements under the USP paddle method of 50 rpm in 900 ml aqueous buffer at pH 4 at 37° C. is from about 95% to about 99% after about 1 hour.

10. A pharmaceutical dosage form according to claim 2 wherein the controlled release component comprises from about 10 to about 200 mg of carbidopa and from 25 to about 600 mg levodopa.

11. A pharmaceutical dosage form according to claim 2 wherein the controlled release component comprises from about 25 to about 150 mg of carbidopa and from 50 to about 500 mg levodopa.

12. A pharmaceutical dosage form according to claim 2 wherein the controlled release component comprises from about 25 to about 50 mg of carbidopa and from 50 to about 200 mg levodopa.

13. A pharmaceutical dosage form according to claim 2 wherein the immediate release component comprises from about 5 to about 75 mg of carbidopa and from 25 to about 300 mg levodopa.

14. A pharmaceutical dosage form according to claim 2 wherein a percentage of the total amount of carbidopa is replaced by another decarboxylase inhibitor.

15. A pharmaceutical dosage form according to claim 2 wherein some or all of the levodopa is in the form of the pro-drug 3-hydroxy-L-tyrosine ethyl ester.

16. A pharmaceutical dosage form according to claim 2 wherein the dosage form is comprised of particles.

17. A pharmaceutical dosage form according to claim 1 wherein the dosage form is comprised of a tablet.

18. A pharmaceutical dosage form according to claim 2 wherein the dosage form is comprised of a bilayer tablet.

19. A pharmaceutical dosage form according to claim 2 wherein the amount of carbidopa in the dosage form is selected from the group consisting of 12.5, 25, 50, 75 and 100 mg.

20. A pharmaceutical dosage form according to claim 2 wherein the amount of levodopa in the dosage form is selected from the group consisting of 25, 37.5, 50, 70, 75, 80, 100, 125, 130, 150, 200, 250, 300, and 400 mg.

21. A pharmaceutical dosage form according to claim 2 wherein the total amount of carbidopa to levodopa in the dosage form is 50 mg/100 mg with the carbidopa to levodopa amount in the immediate release portion being 25 mg/50 mg and the carbidopa to levodopa amount in the controlled release portion being 25 mg/50 mg.

22. A pharmaceutical dosage form according to claim 2 wherein the total amount of carbidopa to levodopa in the dosage form is 50mg/150 mg with the carbidopa to levodopa amount in the immediate release portion being 25 mg/70 mg and the carbidopa to levodopa amount in the controlled release portion being 25 mg/80 mg.

23. A pharmaceutical dosage form according to claim 2 wherein the total amount of carbidopa to levodopa in the dosage form is 50 mg/200 mg with the carbidopa to levodopa amount in the immediate release portion being 25 mg/70 mg and the carbidopa to levodopa amount in the controlled release portion being 25 mg/130 mg.

24. A pharmaceutical dosage form according to claim 2, wherein said immediate release component is in the form of a coating on a solid dosage form; and said controlled release component makes up the solid dosage form, said controlled release component including a retarding agent of a type and amount sufficient to provide the release of active ingredient for a period of from about 1 hour to about 24 hours.

25. A method of treating a patient suffering from a pathology or diseases characterized by reduced levels of dopamine in a patients brain comprising the step of administering to the patient a dosage form according to any of claims 1, 2, 21 or 22.

26. The pharmaceutical dosage form according to claim 2 wherein the dosage form is a matrix dosage form.

27. The pharmaceutical dosage form according to claim 26 wherein the dosage form is a bilayer tablet.

28. The pharmaceutical dosage form according to claim 2 wherein the dosage form includes immediate release particles in combination with controlled release particles.

29. The pharmaceutical dosage form according to claim 28 wherein the immediate release particles and controlled release particles are within an immediate release gelatin capsule.

30. The pharmaceutical dosage form according to claim 28 wherein the immediate release particles and controlled release particles are in the form of a two-layer tablet.

31. The pharmaceutical dosage form according to claim 2 wherein the in vitro release rate is chosen such that the initial peak plasma level of levodopa obtained in vivo occurs between 0.1 and 2 hours after administration of the dosage form to a patient.

* * * * *